United States Patent [19]

DeLuca et al.

[11] 4,265,822

[45] May 5, 1981

[54] PROCESS FOR PREPARING 1-HYDROXYLATED VITAMIN D COMPOUNDS FROM 5,6-TRANS-VITAMIN D COMPOUNDS

[75] Inventors: Hector F. DeLuca; Heinrich K. Schnoes; David E. Hamer, all of Madison; Herbert E. Paaren, Verona, all of Wis.

[73] Assignee: Wisconsin Alumni Research Foundation, Madison, Wis.

[21] Appl. No.: 73,840

[22] Filed: Sep. 10, 1979

[51] Int. Cl.$^3$ .............................................. C07J 9/00
[52] U.S. Cl. .................................. 260/397.2; 204/159
[58] Field of Search ...................................... 260/397.2

[56] References Cited

U.S. PATENT DOCUMENTS 4,195,027  3/1980  DeLuca et al. ................... 260/397.2

OTHER PUBLICATIONS

Steroids, Aug. 1977, vol. 30, No. 2, pp. 193–199.

*Primary Examiner*—Elbert L. Roberts
*Attorney, Agent, or Firm*—Howard W. Bremer

[57] ABSTRACT

A method for preparing 1α-hydroxylated vitamin D compounds from 5,6-trans-vitamin D compounds which comprises allylically oxidizing a 5,6-trans-vitamin D compound, subjecting the oxidation product to actinic radiation in the presence of a photosensitizing agent and recovering the 1α-hydroxylated compound.

1α-hydroxylation is recognized as being essential to impart biological activity to vitamin D compounds and their derivatives. The present invention provides an efficient method for maximizing the yield of 1α-hydroxylated vitamin D compounds.

11 Claims, No Drawings

PROCESS FOR PREPARING 1-HYDROXYLATED VITAMIN D COMPOUNDS FROM 5,6-TRANS-VITAMIN D COMPOUNDS

The invention described herein was made in the course of work under a grant or award from the Department of Health, Education, and Welfare.

DESCRIPTION

1. Technical Field

This invention relates to the preparation of compounds characterized by vitamin D-like activity. More specifically, this invention relates to 1-hydroxylated vitamin D compounds.

The D vitamins (i.e. vitamin $D_3$ or vitamin $D_2$) are well-known agents for the control of calcium and phosphorus homeostasis. In the normal animal these compounds are known to stimulate intestinal calcium absorption and bone-calcium mobilization, and are effective in preventing rickets. It is also well known that to be effective, vitamin $D_3$ (or vitamin $D_2$) must be converted in vivo to its hydroxy-forms. For example, vitamin $D_3$ is first hydroxylated to 25-hydroxyvitamin $D_3$ in the liver, and this intermediate is then further hydroxylated in the kidney to 1α,25-dihydroxyvitamin $D_3$. Vitamin $D_2$ undergoes the same metabolic conversions. The 1α-hydroxylated form of the vitamin is generally considered to be the physiologically active or hormonal form of the vitamin and to be responsible for the various physiological responses mentioned above. It has also been shown that certain unnatural synthetic 1α-hydroxyvitamin D analogs exhibit high biological potency, which in some cases approaches that of the natural forms produced in vivo. Well-known examples are 1α-hydroxyvitamin $D_3$ (U.S. Pat. No. 3,741,996) and 1α-hydroxyvitamin $D_2$ (U.S. Pat. No. 3,907,843) and 3-deoxy-1α-hydroxyvitamin $D_3$ (U.S. Pat. No. 3,906,014).

2. Background Art

Because of the high biological activity of such 1-hydroxylated vitamin D compounds and their potential utility for the treatment of many diseases related to calcium metabolism disorders there has been much interest in chemical processes for their preparation. Almost all of the reported syntheses involve the 1α-hydroxylation of suitable steroids (such as cholesterol) which are subsequently converted to the desired 1α-hydroxyvitamin D compounds (see Schnoes and DeLuca, in Bioorganic Chemistry, vol. 2, Chapter 12, pp. 299–335, edited by E. E. van Tamalen, Academic Press, Inc., New York, 1978).

An interesting alternative process has recently been introduced which provides for the direct C-1-hydroxylation of preformed vitamin D compounds. Pelc (Steroids 30, 193 (1977)) and Paaren et al (Proc. Nat. Acad. Sci. USA 75, 2080 (1978)) have described the preparation of 1α-hydroxyvitamin $D_3$, respectively. However, in this direct oxidation process the yields of desired 1α-hydroxyvitamin D compounds are low, the bulk of the materials obtained being undesired products which must be removed by careful and extensive chromatography.

3. Disclosure of Invention

A new process has now been developed which provides for the efficient preparation of 1α-hydroxyvitamin D compounds (i.e., having the 5,6-cis double bond geometry) from 5,6-trans-vitamin D compounds. This process comprises two steps, namely, the allylic oxidation of 5,6-trans-vitamin D starting materials, with $SeO_2$ being the preferred oxidizing agent, followed by irradiation of the resulting 1-hydroxylated product in the presence of a photosensitizer. Conversion to the desired 1α-hydroxyvitamin D compounds is accomplished in ca. 20–30% yield from the 5,6-trans-vitamin D starting materials by this process.

Best Mode for Carrying Out the Invention

Suitable starting materials for this process are 5,6-trans-vitamin D compounds having the general structure below

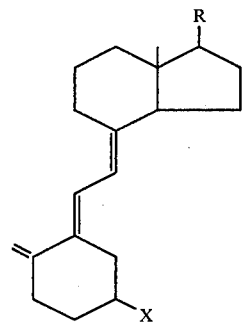

where X is hydrogen, hydroxy or protected hydroxy (e.g., the O-acyl group). The substitutent R in the above structure may be hydrogen or lower alkyl, or may represent any of the common saturated or unsaturated steroid side chains. These side chains may also carry functional groups such as hydroxy, keto, acid or ester groups, as for example the side chains of cholenic acid, or its esters, homocholenic acid, or its esters, 25-keto- or 24-ketocholesterol. In the preferred embodiment, R in the above structure is a steroid side chain having the general structure

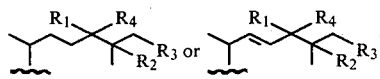

where each of $R_1$, $R_2$, and $R_3$ is selected from the group consisting of hydrogen, hydroxy, lower alkyl or fluoro and where $R_4$ is hydrogen or lower alkyl. Hydroxy functions, if present in the starting material (e.g. at C-3 and/or in the side chain) may also be acylated (e.g. be present as acetates, propionates, butyrates, benzoates, nitro- or halo-benzoates, etc.) or alkylated (e.g. O-methyl, O-ethyl, O-isopropyl, etc.), or be otherwise prevented from reacting with reagents during the course of the process, i.e., protected, as is well-known in the art, by common hydroxy protecting groups. However, such protection is not required for the process of this invention.

As used in this specification and in the claims, "lower alkyl" denotes a hydrocarbon radical of from 1 to about 5 carbons, having a straight chain or branched chain configuration, e.g. methyl, ethyl, propyl, isopropyl, butyl, etc., and the word "acyl" denotes an aliphatic acyl group of from 1–5 carbons, e.g. acetyl, propionyl, butyryl, or an aromatic acyl group, such as benzoate, nitrobenzoate, chlorobenzoate, etc.

A preferred reagent for allylic oxidation of these 5,6-trans-vitamin D starting materials is selenium dioxide. The presence of a hydroperoxide (e.g. hydrogen peroxide, or an alkylhydroperoxide, such as t-butyl hydroperoxide) and of an organic nitrogenous base during oxidation is beneficial. Suitable bases are for example, pyridine, or substituted pyridines (e.g. the isomeric picolines, collidine, octahydroacridine, quinoline) or imidazole or substituted pyrazoles (e.g. 3,5-dimethylpyrazole). An advantageous combination of reagents is, for example, selenium dioxide, t-butylhydroperoxide and octahydroacridine. The reaction is preferably conducted in a solvent, e.g., halocarbon solvents, such as methylene chloride, chloroform, carbon tetrachloride, 1,2-dichloroethane, or 1,3-dichloropropane, at room temperature. At room temperature the reaction is rapid and normally completed within 10–20 minutes although a temperature range from ca. −15° to ca. 30° C. may be used.

The resultant product which, optionally, may be purified by chromatography, is then subject to photochemical conversion.

The photochemical conversion step is effectively conducted by subjecting a solution of the oxidation product to actinic rays in the presence of a photosensitizer. A light source emitting radiation suitable for the excitation of the photosensitizer is effective, provided that light of wave length less than about 310 nm is excluded, either by suitable filters or by choosing a light source which does not emit radiation below that wave length. In practice, it is convenient to use standard commercial fluorescent lamps for the irradiation, such as the commercial cool white, Models FC12T10/CW, FC8T9/CW, F6T5/CW or F15T8D (all manufactured by Westinghouse Electric Corporation), with suitable filters to effectively eliminate the low ultraviolet radiation component. Pyrex glass is a suitable filter and irradiation of the solution contained in a reaction vessel made of standard Pyrex glass is therefore a practical and advantageous procedure for accomplishing this reaction. Suitable solvents for the oxidation product are, for example, benzene or toluene and effective photochemical sensitizers are anthracene, acridine, or phenazine.

It is desirable that the solution be maintained under an inert atmosphere (e.g. nitrogen or argon). The irradiation is preferrably conducted at a temperature below 10° C., with the process of the reaction (i.e. formation of 1-hydroxyvitamin D compounds) being monitored periodically by suitable chromatographic methods, e.g. thin layer chromatography. About 5–10 hours is normally required for completion of the reaction. By way of example, the photochemical conversion can be effectively accomplished by irradiating a toluene solution of the oxidation product reaction mixture containing anthracene as a photosensitizer (in about 40-fold molar excess over the vitamin compound) under a nitrogen atmosphere in the cold room at 4° C. with two commercial circular fluorescent lamps (ca. 50 watt total) suitably arranged around a standard round bottom flask reaction vessel for about 8–10 hours. A high ratio of sensitizer to vitamin compound (e.g. 30–50-fold molar excess) and low temperatures facilitate the reaction. Where benzene is used as solvent temperature above 5° C. is suggested to avoid freezing of solvent. Toluene which can be used below 5° C. is preferred as solvent.

The desired product from the irradiation is readily isolated by evaporating the solvent and chromatography. It is often advantageous to remove the bulk of photosensitizer prior to chromatography, e.g. by redissolving the product in a solvent in which the photosensitizer is sparingly soluble (e.g. an alcohol in the case of anthracene) and removing the photosensitizer by filtration. The resulting filtrate contains a mixture of 1α-hydroxy-vitamin D compound and some 1β-hydroxyvitamin D epimer. These compounds are conveniently separated by chromatography (e.g. column chromatography, thin-layer chromatography, or high pressure liquid chromatography) which also removes any residual sensitizer, to obtain in pure form, the 1α-hydroxyvitamin D compound of general formula below where R and X represent substituents as defined earlier.

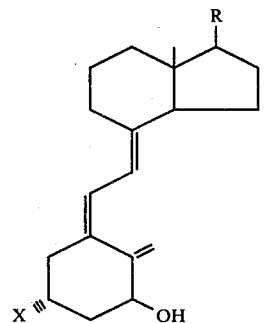

Any hydroxy-protecting groups (e.g. acyl groups) that may be present can be removed if desired, in a final hydrolysis or reduction step using standard and well-known conditions, e.g. hydrolysis with 0.1 M KOH/MeOH at 25°–60° for 1–4 hours, or reduction with lithium aluminum hydride at room temperature for 0.5–1 hour. Alternatively, removal of such hydroxy-protecting groups can also be accomplished at an intermediate stage, i.e. before the photochemical reaction step.

Previously reported methods for the preparation of 1α-hydroxyvitamin D compounds by direct allylic oxidation of vitamin D starting materials (see Pelc, and Paaren et al references cited above) suffer from low yield and are complicated by the formation of a multiplicity of products. The product mixtures obtained by these methods, include, for example, 1α-and 1β-hydroxy-5,6-cis and 5,6-trans-vitamin D, as well as a number of other oxidation products which account for most of the total product recovered.

A particularly advantageous feature of the present two-step process, i.e., oxidation followed by photochemical conversion, is that only 1-hydroxylated vitamin D compounds are obtained and that the desired 1α-hydroxyvitamin D compound is the major product. The present process thus provides for the efficient and simple conversion of 5,6-trans-vitamin D compounds to 1α-hydroxyvitamin D compounds (5,6-cis double bond configuration). Another advantageous aspect of the process is its generality, being applicable to 5,6-trans-vitamin D starting materials bearing any of the common steroid side chains. For example, allylic oxidation and subsequent irradiation of 5,6-trans-vitamin $D_3$ and 5,6-trans-vitamin $D_2$ yields the corresponding 1α-hydroxyvitamin $D_3$ and 1α-hydroxyvitamin $D_2$ products, respectively. The same process applied to 5,6-trans-25-hydroxyvitamin $D_3$ or 5,6-trans-25-hydroxyvitamin $D_2$ provides 1α,25-dihydroxyvitamin $D_3$ and 1α,25-dihydroxyvitamin $D_2$, respectively, and the oxidation and subsequent irradiation of 5,6-trans-24,25-dihydroxyvitamin $D_3$ or 5,6-trans-25,26-dihydroxyvitamin $D_3$ gives 1α,25-trihydroxyvitamin $D_3$ and 1α,25,26-trihydroxyvitamin $D_3$, respectively, in good yield.

The invention is further described by the following Examples which are illustrative only and not to be construed as limiting of the attached claims.

EXAMPLE 1

Synthesis of 1α-hydroxyvitamin $D_3$ from 5,6-trans-vitamin $D_3$: To a 10 ml round-bottomed flask is added 152 mg (1.37 mmol) of selenium dioxide followed by 5 ml of dichloromethane. A charge of 750 mg (4.01 mmol) of octahydro-acridine is added to the above suspension followed by 300 μl of dry t-butylhydroperoxide. The resulting solution is stirred at room temperature for 30 min then 100 mg (0.26 mmol) of solid 5,6-trans-vitamin $D_3$ is added. The reaction mixture is stirred at room temperature under nitrogen atmosphere for 16 min then worked up by pouring into a mixture of 70 ml of ether and 15 ml of 10% aqueous sodium hydroxide. After phase separation the ether layer is washed with 10% sodium hydroxide (5 ml, 1X), water (5 ml, 2X), 1% aqueous acetic acid (5 ml, 2X), water (5 ml, 3X), 10% aqueous sodium hydroxide (5 ml, 1X) and water (5 ml, 3X). After evaporation of the solvent 108.1 mg of crude product is recovered. The crude product is chromatographed on a 1×50 cm silica gel (Silicar CC-7) column with ether as the eluting solvent. The column fractions are assayed by TLC and those fractions containing material of similar polarity to 1-hydroxylated vitamin $D_3$ compounds are pooled to give a crude fraction weighing 54.5 mg after evaporation of the solvent. A major portion (47.0 mg, 86%) of this crude fraction is transferred to a double-walled, water cooled, quartz emission well. To the quartz irradiation apparatus is added 610 mg (3.42 mmol) of anthracene and 150 ml of benzene. After degassing, irradiation (under nitrogen atmosphere at 5° C.) is begun using a 15 Watt, cool-white, tubular fluorescent light bulb. After 13 hours at 6°–7° C., the light is then switched off and the solvent evaporated. The residue is suspended in ethanol and filtered. The filtrate is evaporated and the crude residue of the filtrate is applied to a 1×50 cm silica gel (Silicar CC-7) column. Elution of the column with 1% methanol in chloroform followed by pooling and evaporation of those fractions containing material cochromatographing with a known sample of 1α-hydroxyvitamin $D_3$ yields 24.0 mg (27% yield) of a colorless oil shown to be identical with 1α-hydroxyvitamin $D_3$ by comparison of the sample's nmr, uv, and mass spectra with those of an authentic sample of this compound. The sample cochromatographs with a known sample of 1α-hydroxyvitamin $D_3$ (prepared from 1α-hydroxycholesterol) on silica gel TLC (2.5% methanol in chloroform, or alternatively, ether as eluting solvents).

EXAMPLE 2

Synthesis of 1α-hydroxyvitamin $D_2$ from 5,6-trans-vitamin $D_2$: A solution of 100 mg of 5,6-trans-vitamin $D_3$ in methylene chloride is subjected to allylic oxidation exactly as described in Example 1. The resulting 1-hydroxylated product mixture is recovered as described in the above example and subjected directly to irradiation under the following conditions: to a toluene solution (150 ml) of the product contained in a standard 250-ml-round-bottom flask, is added a 20-fold excess of anthracene as photo-sensitizer. The solution is degassed and placed under a nitrogen atmosphere. It is then irradiated with two commercial circular fluorescent lamps (Westinghouse Models FC12T10/CW (32 Watt) and FC8T9/CW (22 Watt)) placed around the flask, for 9 hours; the solution is maintained at 4° C. during irradiation. The product is isolated by addition of isopropanol and azeotropic evaporation of solvent, addition of ethanol to the residue and filtration of the anthracene. Chromatography of the residue remaining after evaporation of ethanol solvent on a silica gel column (1×50 cm) eluted with 1% methanol in $CHCl_3$, gives the desired 1α-hydroxyvitamin $D_2$ in 25% overall yield. The product is identical with an authentic sample in its chromatographic and spectroscopic properties.

What is claimed is:

1. In a process for preparing 1α-hydroxylated vitamin D compounds comprising allylically oxidizing a vitamin D compound utilizing $SeO_2$ as the oxidant and exposing the oxidized product to actinic radiation, the improvement which comprises
   utilizing a 5,6-trans vitamin D compound corresponding to the 1α-hydroxylated vitamin D compound which it is desired to obtain as the vitamin D compound subjected to the allylic oxidation
   conducting the allylic oxidation in the presence of an organic nitrogenous base
   exposing the oxidation products to actinic radiation having a wave length greater than about 310 nm in the presence of a photosensitizing agent and
   recovering the 1α-hydroxylated vitamin D compound.

2. The process of claim 1 wherein the allylic oxidation is conducted in the presence of a hydrogen peroxide or alkylhydroperoxide.

3. The process of claim 1 wherein the nitrogenous base is selected from pyridine, alkyl-substituted pyridines, quinoline, imidazole or alkyl-substituted pyrazoles.

4. The process of claim 1 wherein the photosensitizer is selected from the group consisting of anthracene, phenazine, and acridine.

5. The process of claim 1 wherein the 5,6-trans-vitamin D compounds submitted to allylic oxidation have the formula

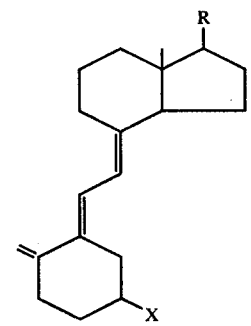

where X is selected from hydrogen, hydroxy or protected hydroxy and R is a steroid side chain selected from the following configurations

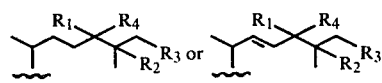

where each of $R_1$, $R_2$, and $R_3$ is selected from the group consisting of hydrogen, hydroxy, protected-hydroxy, lower alkyl and fluoro, and where $R_4$ is hydrogen or lower alkyl.

6. The process of claim 5 where the 5,6-trans-vitamin D compound submitted to allylic oxidation is 5,6-trans-vitamin $D_3$.

7. The process of claim 5 where the 5,6-trans-vitamin D compound submitted to allylic oxidation is 5,6-trans-25-hydroxyvitamin $D_3$.

8. The process of claim 5 where the 5,6-trans-vitamin D compound submitted to allylic oxidation is 5,6-trans-vitamin $D_2$.

9. The process of claim 5 where the 5,6-trans-vitamin D compound submitted to allylic oxidation is 5,6-trans-25-hydroxyvitamin $D_2$.

10. The process of claim 5 where the 5,6-trans-vitamin D compound submitted to allylic oxidation is 5,6-trans-24,25-dihydroxyvitamin $D_3$.

11. The process of claim 5 where the 5,6-trans-vitamin D compound submitted to allylic oxidation is 5,6-trans-24-hydroxyvitamin $D_3$.

* * * * *